US007347825B2

(12) United States Patent
Vaughan et al.

(10) Patent No.: US 7,347,825 B2
(45) Date of Patent: Mar. 25, 2008

(54) DEVICE AND METHOD FOR ASSESSING ASTHMA AND OTHER DISEASES

(75) Inventors: John W. Vaughan, Charlottesville, VA (US); John F. Hunt, Charlottesville, VA (US); Benjamin M. Gaston, Charlottesville, VA (US); Timothy L. Macdonald, Charlottesville, VA (US)

(73) Assignee: University of Virginia Patent Foundation, Charlottesville, VA (US)

( * ) Notice: Subject to any disclaimer, the term of this patent is extended or adjusted under 35 U.S.C. 154(b) by 807 days.

(21) Appl. No.: 10/474,979

(22) PCT Filed: Apr. 17, 2002

(86) PCT No.: PCT/US02/15250

§ 371 (c)(1),
(2), (4) Date: Oct. 16, 2003

(87) PCT Pub. No.: WO02/082977

PCT Pub. Date: Oct. 24, 2002

(65) Prior Publication Data

US 2004/0127808 A1   Jul. 1, 2004

Related U.S. Application Data

(60) Provisional application No. 60/284,155, filed on Apr. 17, 2001.

(51) Int. Cl.
*A61B 5/02* (2006.01)
*G01N 1/22* (2006.01)
*G01N 31/00* (2006.01)
*G01N 33/497* (2006.01)
*B32B 5/02* (2006.01)
*B32B 27/04* (2006.01)
*B32B 27/12* (2006.01)

(52) U.S. Cl. ................ 600/532; 73/23.3; 422/84

(58) Field of Classification Search ................ None
See application file for complete search history.

(56) References Cited

U.S. PATENT DOCUMENTS 5,081,871 A   1/1992 Glaser (Continued)

FOREIGN PATENT DOCUMENTS

EP   0759169   11/1995

OTHER PUBLICATIONS

Kharitonov, S.A., "Exhaled Markers of Pulmonary Disease," American Journal of Respiratory Critical Care Medicine, 163 ed., vol. 163 (No. 7), p. 1693-772, (2001).

(Continued)

*Primary Examiner*—Robert Nasser
(74) *Attorney, Agent, or Firm*—Robert J. Decker

(57) ABSTRACT

Device and method for non-invasively monitoring asthma and other respiratory diseases, as well as non-respiratory diseases. The method includes collecting condensate from a subject's breath, testing the condensate to determine its acetic acid/acetate level or concentration, and evaluating these properties to determine the presence, absence or status of a respiratory or non-respiratory disease in the subject. The method may also include, prior to the testing step, standardizing the volatile substances that may be present within the condensate in a degassing or gas standardizing step. The device includes a mouthpiece apparatus configured to receive breath from a subject, a condensation apparatus to condense the subject's breath and produce a condensate, and a collection apparatus having a collection chamber containing means for testing the condensate to determine the acetic acid and/or acetate concentration. The device may also include a system for removing or standardizing the volatile substances that may be present with the condensate. The device and method may be utilized without condensing a subject's breath and collecting the same.

71 Claims, 5 Drawing Sheets

U.S. PATENT DOCUMENTS

| | | | |
|---|---|---|---|
| 5,922,610 | A | 7/1999 | Alving |
| 6,585,661 | B1 * | 7/2003 | Hunt et al. .................. 600/532 |
| 6,930,125 | B2 * | 8/2005 | Hunt et al. .................. 514/423 |
| 7,118,537 | B2 | 10/2006 | Baddour |

OTHER PUBLICATIONS

Hunt, J.F., "Endogenous Airway Acidification. Implications for Asthma Pathophysiology," American Journal of Respiratory Care Medicine, vol. 161 (No. 3), p. 694-9, (2000).

Mochizuki, H., "Relationship Between Ultrasonically Nebulized Distilled Water-Induced Brochoconstriction and Acetic Acid-Induced Cough in Asthmatic Children," Journal of Allergy & Clinical Immunology, vol. 96 (No. 2), p. 193-9, (1995).

Shimizu, T., "Relationship Between the Acid-Induced Cough Response and Airway Responsiveness and Obstruction in Children with Asthma," Thorax, vol. 51 (No. 3), p. 284-7, (1996). (Abstract only).

Fine, J.M., "The Roles of pH and Iconic Species in Sulfur Dioxide- and Sulfite-Induced Bronchoconstriction," American Review of Respiratory Disease, vol. 136 (No. 5), p. 1122-6, (1987). (Abstract only).

Ohrui, T., "Mechanisms of Gastric Juice-Induced Hyperpermeability of the Cultured Human Tracheal Epithelium," Chest, vol. 111 (No. 2), p. 454-9, (1997).

Holma, B., "pH Effects on Ciliomotility and Morphology of Respiratory Mucosa," Archives of Environmental Health, vol. 32 (No. 5), p. 216-26, (1977). (Abstract only).

Luk, C.K., "Effect of pH, Viscosity and Ionic-Strength Changes on Ciliary Beating Frequency of Human Bronchial Explants," Clinical Science, vol. 64 (No. 4), p. 449-51, (1983). (Abstract only).

Holma, B., "pH-and Protein-Dependent Buffer Capacity and Viscosity of Respiratory Mucus. Their Interrelationships and Influence on Health," The Science of the Total Environment, p. 71-82, (1989). (Abstract only).

Ward, C., "The origin of Water and Urea Sampled at Bronchoalveolar Lavage in Asthmatic and Control Subjects," American Review of Respiratory Disease, vol. 146 (No. 2), p. 444-7, (1992). (Abstract only).

Holz, O., "Update on Sputum Methodology," European Respiratory Journal, vol. 16 (No. 2), p. 355-9, (2000).

Gershman, N.H., "Fractional Analysis of Sequential Induced Sputum Samples During Sputum Induction: Evidence that Different Lung Compartments are Sampled at Different Time Points," Journal of Allergy & Clinical Immunology, vol. 104 (No. 2), p. 322-8, (1999). (Abstract only).

de Jongste, T.C., "Control of Airway Caliber by Autonomic Nerves in Asthma and in Chronic Obstructive Pulmonary Disease.," American Review of Respiratory Disease, vol. 143 (No. 6), p. 1421-6, (1991). (Abstract only).

Gleich, G.J., "Eosinophil-Associated Inflammation in Bronchial Asthma: A Connection to the Nervous System," International Archives of Allergy and Immunology, vol. 107, (No. 1), p. 205-7, (1995). (Abstract only).

Liu, L., "A Metabolic Enzyme for S-Nitrosothiol Conserved From Bacteria to Humans," Nature, vol. 410 (No. 682), p. 490-4, (2001). (Abstract only).

Fang, K, "S-Nitrosoglutathione Breakdown Prevents Airway Smooth Muscle Relaxation in the Guinea Pig," American Journal of Physiology and Lung Cell Molecular Physiology, vol. 279 (No. 4), p. L716-21, (2000). (Abstract only).

Altura, B.M., "Failure of Acetaldehyde or Acetate to Mimic the Splanchnic Arterilar or Venular Dilator Actions of Ethanol: Direct in situ Studies on the Microcirculaltion," British Journal of Pharmacology, vol. 73 (No.3), p. 580-2, (1981). (Abstract only).

* cited by examiner

DEVICE AND METHOD FOR ASSESSING ASTHMA AND OTHER DISEASES

CROSS-REFERENCE TO RELATED PROVISIONAL APPLICATION

The present application is a national stage filing of International Application No. PCT/US02/US02/15250, filed 17 Apr. 2002, which claims the benefit under 35 U.S.C. Section 119(e) of the earlier filing date of U.S. Provisional Patent Application Ser. No. 60/284,155, filed Apr. 17, 2001, which are hereby incorporated by reference herein in their entirety. The present application is also related to U.S. patent application Ser. No. 09/857,820, now U.S. Pat. No. 6,585,661, which is a national stage filing of International Application No. PCT/US99/30184, filed Dec. 17, 1999, which are hereby incorporated by reference herein in their entirety.

GOVERNMENT SUPPORT

Work described herein was supported by Federal Grant No. R01 8L59337-01, awarded by the National Institutes of Health. The United States government possesses certain rights in and to this invention.

FIELD OF THE INVENTION

The present invention relates to a device and method for non-invasively monitoring diseases. More particularly, the present invention relates to a device and method for determining the acetic acid and acetate concentrations of exhaled breath to detect, diagnose and treat a variety of respiratory, and non-respiratory diseases.

BACKGROUND OF THE INVENTION

Asthma is a chronic inflammatory disorder of the airways affecting the world population in epidemic proportions. Indeed, approximately five percent of the world population is affected. This means that over 15 million Americans, and hundreds of millions of others worldwide, are susceptible. In the United States, over 400,000 hospitalizations for asthma were required during 1994, and over 1.9 million asthma related emergency room visits were made during 1995. Over 5,000 asthma related deaths occur in the United States each year. See http://www.asthmainamerica.com (Oct. 15, 1999).

In susceptible individuals, asthma causes recurrent episodes of coughing, wheezing, chest tightness, and difficult breathing. Inflammation makes airways sensitive to stimuli such as allergens, chemical irritants, tobacco smoke, cold air and exercise. When exposed to such stimuli, airways may become swollen, constricted, filled with mucus, and hyper responsive to stimuli.

There currently is no cure for asthma, but two types of treatments that suppress asthma symptoms and prevent attacks are currently used by many asthma sufferers. One of these types of treatments employs quick-relief medications, such as inhaled bronchodilator therapy, which works quickly to suppress symptoms by relaxing airway smooth muscle. The other of these types of treatments employs long-term preventive medications, such as inhaled, oral, or intramuscular corticosteroids, and leukotriene antagonists, which can prevent the onset of symptoms and attacks by controlling the underlying inflammation, thereby keeping persistent asthma under control. Unfortunately, many of the preventive medications have undesirable side effects, such as serious as growth limitation in children, osteoporosis, weight gain, and cataracts. As a result, the failure to properly identify the amount of inflammation in the airways, and therefore the appropriate treatment for a subject' asthmatic condition, may significantly adversely impact the subject' health. To date, however, there is no generally accepted manner of readily determining whether a given patient requires treatment, let alone what specific type of treatment should be used.

Conventionally, asthma is diagnosed by examining a number of indicators and qualitatively assessing the observed results. For example, a clinical diagnosis of asthma is often prompted by a combination of symptoms such as episodic breathlessness, wheezing, chest tightness, and coughing. However, these symptoms often occur only nocturnally and therefore are difficult for a doctor to monitor or measure. In addition, recently manifested symptoms alone are neither diagnostic indicators for asthma nor true measures of severity, so doctors must often evaluate a patient' health over long time periods before a diagnosis of asthma may be made with reasonable confidence. Because of the difficulty inherent in diagnosing asthma, doctors must use a patient's response to asthma treatments as a diagnostic tool. For example, the fact that bronchodilator treatment results in the relief of symptoms generally associated with asthma could indicate the presence of asthma. Disadvantageously, such diagnosis methods may result in the unnecessary application of asthma medications that have undesirable side effects. Accordingly, it would be desirable to have a device and method for readily diagnosing asthma before engaging in a course of treatment.

After a physician has covered the difficult ground of determining whether a person suffers from asthma, the physician must go through another process to determine the degree of severity of the asthma in order to prescribe an appropriate course of treatment. As with the diagnosis of asthma generally, there currently is no simple or noninvasive way to measure the degree of inflammation. There also is no objective method for determining when a course of treatment for airway inflammation can be discontinued. Accordingly, it would be desirable to have a device and method for simply, non-invasively and accurately determining the degree or severity of an asthmatic condition, and to what degree, if at all, a chosen course of treatment will be, or has been, effective.

In the past, few devices and methods for diagnosing asthma have been proposed, and those that have been proposed have not met with success. U.S. Pat. No. 5,922,610 to Alving, et al., issued Jul. 13, 1999, discloses a system and method for diagnosing inflammatory respiratory disorders related to abnormal nitric oxide (NO) levels in exhaled breathing air. The approach of the '610 patent includes a mask into which a subject may breathe, filters for removing substances present in the exhaled air that may interfere with NO measurement, and an instrument which receives the uncondensed exhaled air and uses a chemiluminescence technique to measure the NO level of the exhalate. The approach of the '610 patent therefore is very different from that of the present invention, which is drawn to diagnosing and treating respiratory diseases such as asthma by monitoring the acetic acid concentrations of breath samples, including exhaled breath condensate samples exhalate.

Other devices and methods have been proposed which collect a breath sample for diagnostic purposes, but like the '610 patent, none of these proposals teach or suggest testing a breath sample for acetic acid/acetate concentrations to diagnose asthma or other respiratory or other diseases. For example, European Patent No. 0759169, published Nov. 23, 1995 (published with English translation of claims only), discloses a process and device for collecting expired breath content, which may later be evaluated to determine the condition and metabolic performance of organs such as the lungs and the respiratory system. Among other significant differences between the present invention and the approach of the '169 patent, the latter does not appear to contemplate any specific respiratory disorders, such as asthma, in connection with which the disclosed device and process may be useful, nor does it appear to teach or suggest testing condensed breath exhalate for acetic acid/acetate concentrations as an indicator of any respiratory disease or other disease. Similarly, U.S. Pat. No. 5,081,871 to Glaser, issued Jan. 21, 1992, discloses an apparatus and method for collecting human exhaled breath for later analysis to determine whether the sample contains harmful substances such as volatile solvents, volatile compounds, endogenous compounds, volatile endogenously produced or used compounds, toxic chemicals, organic solvents, and natural air gasses. The '871 patent does not relate to the collection and testing of a breath condensate, nor does it teach or suggest testing exhalate for acidity or ammonium acetic acid/acetate concentrations to diagnose respiratory diseases. In addition, the device and method of the '871 patent are substantially different from those of the present invention.

The ability to monitor conditions in the lung is important in the management of respiratory disease. Currently, peak flow measurements, spirometry and other indirect methods are often used to measure lung function. Results from these tests are used to evaluate the patient's condition and subsequent testing is aimed at monitoring disease progression. Unfortunately, these tests are often effort dependent and open to inconsistent results.

Acetic acid is a volatile compound produced in the airway through a number of pathways. Some pathways include, but are not limited to, eukaryotic acetycholinesterase, and eukaryotic or prokaryotic aldehyde dehydrogenases. One source of acetic acid in the breath is from the breakdown and clearing of ethanol from the body. The presence of acetic acid in the airway of patients with respiratory disease has not been previously described or associated with respiratory disease states.

The present invention is based on the determination that acetic acid and/or acetate levels have a large impact on exhaled breath condensate pH and are involved in the respiratory disease symptoms. In particular, applicants assert that the relative level of acetic acid and/or acetate in the airway can be monitored and used in the diagnosis, management and treatment of respiratory disease.

Other devices for collecting exhaled breath are shown in International Application No. PCT/US01/13895 to Baddour, filed Apr. 30, 2001 and U.S. Pat. No. 6,033,368 to Gaston et al., filed Mar. 28, 1996, which are hereby incorporated by reference herein in their entirety.

SUMMARY OF THE INVENTION

The current definition of asthma is 1) an inflammatory lung disease that consists of 2) recurrent episodes of reversible airway obstruction and 3) bronchial hyperactivity. This is a three-pronged definition that is not particularly useful in the clinical setting now, because of the difficulty of assessing airway inflammation in patients. The Applicants provides a fourth component to the definition of asthma: Airway acidification. Airway acidification, in part caused by excessive acetic acid production, and through a variety of other potential mechanisms, lead to each of the other three parts of the definition. Thus, the Applicants set forth herein that acetic acid is a singularly critical component of airway disease.

Moreover, acidification may be taken into account as secondary to inflammation, as well as a primary cause. First, activated lymphocytes are known to migrate toward low pH regions. Eosinophils—a key cell in the asthmatic airway—suffer rapid pro-inflammatory necrosis at low pH. Additionally, ciliary beating fails, mucous viscosity increases, and many antioxidants become less effective at low pH. All these factors enhance inflammation and airway obstruction.

One object of the invention is to provide a method to diagnose, manage and treat a range of respiratory diseases in humans and animals using assays of acetic acid and/or acetate concentrations in the breath.

In another embodiment of the invention there is a measurable change in acetic acid levels found in the breath after ethanol ingestion. Accordingly, the invention may also be used to monitor environmental exposures that increase acetic acid or alcohol production in humans and animals. This acetic acid/acetate may result from eukaryotic or prokaryotic metabolism of ingested alcohol.

The present invention includes a method and device for monitoring respiratory diseases such as asthma, in a subject, as well as non-respiratory diseases such as systemic inflammatory diseases. Some non-limiting examples include lupus, rheumatoid arthritis, sepsis, and acute respiratory distress syndrome (ARDS). Other respiratory diseases include, but not limited thereto, bronchiolitis, chronic obstructive pulmonary, bronchiectasis, common cold, cystic fibrosis, smoking induced diseases, tuberculosis, occupational lung diseases, pulmonary hypertension, Acute Lung Injury, Acute Respiratory Distress Syndrome, pneumonia, and pulmonary hypertension.

The method generally includes the steps of collecting condensate from a subject's breath, testing the condensate to determine its acetic acid and/or acetate concentration, and evaluating the acetic acid and/or acetate concentration to determine the presence, absence or status of a respiratory and/or non-respiratory disease in the subject. The method may also include, prior to the testing step, standardizing the volatile substances that may be present within the condensate. This may be done by a gas standardizing step or a degassing step. The degassing step may include, for example, introducing an inert gas such as argon or helium to said condensate to remove acidifying carbon dioxide. It is contemplated that many respiratory diseases in humans or other vertebrates may be amenable to monitoring in accordance with the present method, including, for example, inflammatory respiratory diseases such as bronchiolitis, cystic fibrosis, smoking induced diseases, tuberculosis and occupational lung diseases. The method is believed to be particularly applicable to diagnosing and treating asthma.

The step of collecting condensate from a subject's breath may include condensing breath that has been exhaled through the subject's mouth, nose, or both, as well as breath that has been exhaled through the subject's endotrachial tube or tracheostomy tube. This step may further entail introducing the subject's breath into a condensation apparatus, which is capable of condensing the breath, and moving the condensate into a collection apparatus by force of gravity or by mechanical means, such as a pump. Once a breath sample has been received by the condensation apparatus, and preferably after at least a small sample of condensate has been produced by the condensation apparatus, the breath sample may be recirculated through the condensation apparatus until the condensation apparatus has produced a volume of condensate sufficient for the desired testing. In another aspect of the method of the present invention, the collecting step may include, before introducing a breath sample into the condensation apparatus, cooling the condensation apparatus (or one or more parts thereof) in a home freezer or other type of device to cool the condensation apparatus to a temperature lower than that of the condensate to be tested. The temperature to which the condensation apparatus is cooled, depending upon the material limitations of the apparatus, preferably is at least as low as room temperature, and more preferably still 0° C. and even colder. It will be appreciated, however, that the method of the present invention will operate at both higher and lower temperatures.

The step of testing the condensate may include using means for testing the condensate to determine said acetic acid/acetate level. Such means may include, among other things, an electronic or other type of monitor, or a solid, liquid or gaseous reagent introduced to the condensate directly or indirectly. Preferably, the testing step is performed within the collection apparatus using one or more of such methods, or other appropriate methods, eliminating the need to transport the condensate for testing elsewhere.

Alternatively, the condensation and the collection steps may occur in the same general container.

The step of evaluating said acidity level or ammonium concentration to determine the presence, absence or status of a respiratory disease in the subject may include, for example, evaluating the acetic acid and/or acetate concentration to diagnose, determine the severity of, determine a course of treatment for, determine the propriety of altering or discontinuing a course of treatment for, or predicting an impending exacerbation of a respiratory and/or a non-respiratory disease in a subject.

The device of the present invention, which may be used in performing the method of the present invention, generally includes a mouthpiece apparatus configured to receive breath from a subject, a condensation apparatus configured for operative connection to the mouthpiece apparatus and to condense the subject's breath and produce a condensate, and a collection apparatus configured for operative connection to said condensation apparatus and having a collection chamber containing means for testing the condensate to determine its chemical properties. The device may also incorporate or be used in conjunction with an apparatus to standardize volatile substances within the condensate. The device therefore makes it possible to receive, condense, standardize and evaluate a breath sample from a subject in a single device in order to determine the presence, absence or status of a respiratory disease in the subject. In one preferred embodiment, each of the mouthpiece apparatus, condensation apparatus, collection apparatus and collection chamber are separable from each other. More preferably still, the collection chamber is removable and disposable such that, once condensate has been collected therein, the chamber may be shipped to a testing facility. A conventional glass or plastic test tube, for example, would be suitable for many applications as such a disposable collection chamber. The condensation apparatus may include removable insulation, such that the insulation may be removed and the condensation apparatus placed in a home freezer or other cooling device prior to use.

In another preferred embodiment, the condensation apparatus and collection apparatus is defined by the same general chamber.

The mouthpiece apparatus preferably includes a mouthpiece, which may be formed so that a subject may comfortably exhale from the user's mouth and/or nose into the mouthpiece apparatus. The mouthpiece apparatus preferably also includes a first one-way valve configured to permit air to be drawn into the mouthpiece apparatus by a subject, and a second one-way valve configured to permit air to pass from the mouthpiece to a distal end of the mouthpiece apparatus. A particle or other type of filter may be positioned in the mouthpiece apparatus between the mouthpiece and the distal end of the mouthpiece apparatus.

The condensation apparatus of the device of the present invention preferably comprises an inner tube surrounded by an insulator. In one aspect of the invention, the inner tube has an outer surface, and the condensation apparatus further comprises an outer tube disposed between the inner tube and the insulator. In such a configuration, the inner surface of the outer tube and the outer surface of the inner tube preferably define a heat transfer chamber in which a solid, liquid or gas cooling material may be disposed to help cool or insulate the inner tube through which breath exhalate is to pass.

The collection apparatus may have a connector portion configured to connect the condensation apparatus to the collection chamber. The collection chamber preferably includes a measuring gradient, which may be configured for use as a quick reference to determine the volume of condensate that has been collected in the collection chamber during use of the device. The collection chamber also preferably contains means for testing the condensate to determine the chemical properties of the condensate. As described previously in connection with the method of the present invention, such means may include, among other things, an electronic or other type of monitor, or a solid, liquid or gaseous reagent introduced to the condensate directly or indirectly. For example, the collection chamber may have a reagent chamber therein containing one or more reagents. It could be configured so that condensate collects in the collection chamber, eventually coming into contact with the reagent in the reagent chamber, or so that as condensate is produced, it enters the reagent chamber within the collection chamber. Alternatively, the means for testing said condensate may comprise a retainer configured to hold a material, such as cloth or paper, in which one or more reagents are embedded or otherwise contained.

In one aspect of the device of the present invention in which it is configured for determining the acetic acid and/or acetate of a subject's condensate, the means for testing may include, among other things a reagent and an electrode of an electronic monitor, which may optionally be configured to connect to the collection chamber or another part of the device by adhesives, latches, VELCRO, snaps, screw threads or other attachment means. Other testing devices include a mass spectroscopy system, gas chromatography mass spectroscopy system (GCMS), or artificial nose. As one skilled in the art would appreciate, various commercially available artificial noses may be utilized. For example, at Cyrano Sciences, Inc. they are commercializing an electronic nose technology invented at the California Institute of Technology. This technology involves an array of sensors composed of polymers that are filled with conductive particles. When these sensors come in contact with a vapor, the polymer expands changing the resistance of the composite. This change in resistance is transmitted to a computer and the pattern derived from the sensor array is used to determine the type, quantity or quality of the odor that was sensed. This type of information is useful in a wide range of industries including the chemical, automotive, medical, petroleum, food, and fragrances.

The apparatus for standardizing volatile substances within the condensate may comprise a degassing apparatus or a gas standardizing apparatus. The degassing apparatus may include a manual or automatic pump, or a compressed gas container or other apparatus, for drawing or forcing an inert gas through the condensate before or during the measurement of the acetic acid or acetate concentration, or other characteristics of the condensate. The gas standardizing apparatus also may include a pump or compressed gas container or other apparatus for passing atmospheric air through the condensate in a similar manner.

Still further, the present invention comprises a device or method for assessing a disease in a subject, wherein a trapping apparatus is configured for directly trapping a subjects breath without the need for the condensation function/step. The trapping apparatus being comprised of a tube or container (open or closed container) with a reagent substance disposed therein or in communication therewith. For example, the reagent may be located in a relatively open area or on a holder. In one exemplary mode, the exhaled gas bubbles through the reagent or that the reagent fluid has a very high surface area in order to absorb the acetic acid. The reagent substance being effective for trapping acetic acid and/or acetate concentration(s) from said subject's exhaled breath. By allowing the reagent (or sensor device) to directly process the exhalate as it is received in the device, this eliminates the step of collecting or accumulating the condensation. The trapping apparatus may further comprise a device or means for (or may be in communication therewith a means for) testing the trapped acetic acid and acetate to determine concentration(s) thereof. Some non-limiting examples include a spectroscopy system, electrode, chemical reagent strip or artificial nose. An evaluating means for evaluating the acetic acid and/or acetate concentration may be provided for determining the presence, absence or status of a disease in the subject. It will be appreciated that other means for determining properties of the exhalate, such as conducting polymers, may be employed as an alternative to the use of reagents.

The foregoing and other features, objects and advantages of the present invention will be apparent from the following detailed description, taken in connection with the accompanying figures, the scope of the invention being set forth in the appended claims.

BRIEF DESCRIPTION OF THE DRAWINGS

The accompanying drawings, which are incorporated into and form a part of the instant specification, illustrate several aspects and embodiments of the present invention and, together with the description herein, serve to explain the principles of the invention. The drawings are provided only for the purpose of illustrating preferred embodiments of the invention and are not to be construed as limiting the invention. In the drawings.

DETAILED DESCRIPTION OF THE INVENTION

Figure 1:
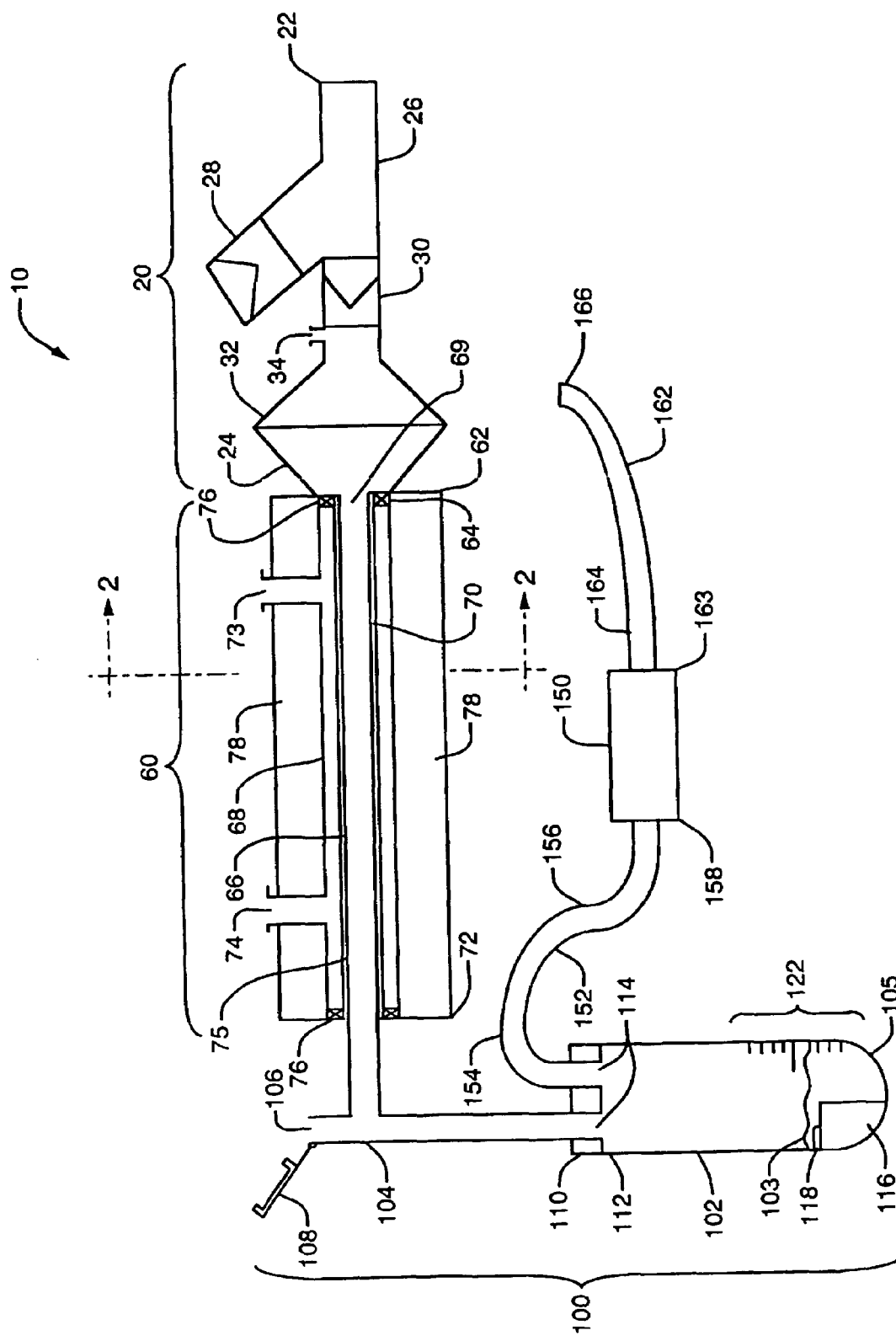
FIG. 1 is a cross-sectional view of one embodiment of the device of the present invention.

Referring now to the drawings, one embodiment of the device of the present invention is illustrated in FIG. 1. As shown in that figure, device 10 of the present invention generally includes a mouthpiece apparatus 20, a condensation apparatus 60, and a collection apparatus 100. Mouthpiece apparatus 20 has a proximal end 22 and a distal end 24, and includes a mouthpiece 26 configured to sealingly engage one or more of a subject's mouth, nose or artificial airway. Although mouthpiece apparatus 20 in FIG. 1 is configured particularly for use with human subjects, the present invention contemplates that it may be configured for use in connection with any other air-breathing beings. In the embodiment of FIG. 1, mouthpiece apparatus 20 also includes a first one-way valve 28, which allows air to be drawn into mouthpiece 26 and into the mouth, nose or artificial airway of an inhaling subject, and a second one-way valve 30, which allows air to exit mouthpiece 26 and enter the remainder of device 10. Mouthpiece apparatus 20 further includes a filter 32 containing a filter element (not shown) which may be selected for eliminating large particles which might originate in the upper airway of a subject, while trapping saliva that could contaminate the exhalate sample. Indeed, the filter element may be selected to have any pore size or electrochemical or other properties so as to gain any desired information regarding condensates derived from different sources within a subject's airway. In FIG. 1, filter 32 is located between second one-way valve 30 and distal end 24 of mouthpiece apparatus 20.

A port 34 may be constructed in mouthpiece apparatus 20 to allow monitoring of airflow, pressure, or other parameters. Mouthpiece apparatus 20 may be constructed from any suitable materials, and is preferably made from commercially available, lightweight plastic and latex components. Preferably, many or all of the components of mouthpiece apparatus 20 are inexpensive, conventional items that are currently commercially available.

At its distal end 24, mouthpiece apparatus 20 attaches to a proximal end 62 of condensation apparatus 60. Preferably, mouthpiece apparatus 20 is configured to be selectively detachable to condensation apparatus 60. Such a design is advantageous because, among other possibilities, filter 32, first and second one-way valves 28 and 30 and other components of mouthpiece 20 may be replaced without replacing condensation apparatus 60, and vice-versa. For similar reasons, it is preferable that the various components of mouthpiece apparatus 20 may be selectively detached from one another. A cap or other valve (not shown) may be used to prevent or regulate communication between filter 32 and condensation apparatus 60.

Condensation apparatus 60 is configured to condense gaseous exhaled breath into a liquid form. In the embodiment of FIG. 1, condensation apparatus 60 includes an inner tube 66 concentrically disposed within an outer tube 68. Inner tube 66 contains a passage 69 extending from a proximal end 64 to a distal end 72 of inner tube 66. Inner tube 66 preferably has a smooth, water repellant inner surface for the easy removal of condensate. The inner diameter of outer tube 68 preferably is larger than the outer diameter of inner tube 66, such that a heat transfer chamber 75 is defined between outer tube 68 and inner tube 66. In the adult model constructed of the embodiment of device 10 of FIG. 1, the length, internal diameter, and wall thickness of inner tube 66 are 12 inches, ⅜ inch, and 1/16 inch, whereas in the child model these dimensions are 12 inches, ¼ inch and 1/16 inch. In the adult model, the length, internal diameter and wall thickness of outer tube 68 are 11 inches, ⅞ inch and 1/16 inch, whereas in the child model these dimensions are 11 inches, ⅞ inch and 1/16 inch. It will be appreciated, however, that these and other dimensions are exemplary only and may be varied to modify the efficiency of condensation apparatus 60.

The materials used to construct inner tube 66 and outer tube 68 are not critical, although they preferably are inexpensive, lightweight and durable. In addition, for reasons that will become apparent, the material used for inner tube 66 preferably is highly heat conductive, whereas the material used for outer tube 68 preferably is highly insulative. In the embodiment of FIG. 1, inner tube 66 is made of finely honed aluminum with a smooth inner surface, and may have a Teflon™ or other water repellent coating. Outer tube 68 is made of a common grade plastic.

A cooling material 70 may be disposed in heat transfer chamber 75 between outer tube 68 and inner tube 66. Cooling material 70 may be a solid, gas or liquid that allows prolonged maintenance of cold temperatures in the condensation apparatus 60. In the embodiment of FIG. 1, for example, cooling material 70 is Coldice Gel Refrigerant™, a high specific heat gel commercially available from Cold ice, Inc. (Oakland, Calif.). In another embodiment, for example, cooling material 70 may be Freon or another chemical. Cooling material 70 also may be a combination of chemicals which, when mixed, produce an endothermic reaction that may be used to cool exhalate moving through tube 66 of condensation apparatus 60 without the need for external cooling. In such a design, condensation apparatus 60 preferably is configured to permit replacement of the chemicals. For example, as shown in FIG. 1, a closeable entry port 73 and exit port 74 may be formed in outer tube 68 for extracting used chemicals and inserting new ones. Although a similar modification may be made to adapt device 10 for the use of an external cooling pump or other such cooling device, there are significant advantages to using an internal cooling system including simplicity and cost.

Outer tube 68 may be designed with integral end caps for retaining cooling material 70 between outer tube 68 and inner tube 66. Alternatively, as shown in FIG. 1, it may be desirable to provide plugs 76 at both ends of outer tube 68 to prevent egress of cooling material 70. Plugs 76 may be composed of rubber, plastic, silicon, metal or any other suitable material. In the embodiment of FIG. 1, for example, plugs 76 are made of a common grade rubber, inserted with plumbing Goop™ made by Eclectic Products, Inc. Cooling material 70 preferably is placed in direct contact with the outer surface of inner tube 66, and does not come into contact with the exhalate moving through tube 66.

Figure 2:
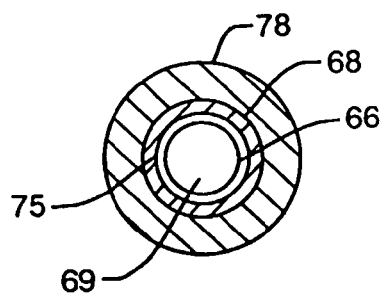
FIG. 2 is a cross-sectional view of the device of FIG. 1 taken along line A-A.

An insulator 78 may be placed around outer tube 68 to extend the effect of cooling material 70 in cooling and condensing exhalate as it passes through condensation apparatus 60. Insulator 78 may be made of materials such as are used commonly in plumbing to insulate pipes, or from other insulating materials. In the embodiment of FIG. 1, insulator 78 is made of foam plastic and has a 5/16 inch thickness, a 10½ inch length, and a 1½ inch outer diameter. Insulator 78 may be designed to be removable from condensation apparatus 60, such as by sliding over the condensation apparatus 60 longitudinally. Alternatively, insulator 78 may be made with a longitudinal slit to permit it to be easily wrapped around, or removed from, condensation apparatus 60. A cross-sectional view taken at line A-A in FIG. 1 is illustrated in FIG. 2.

Collection apparatus 100 is optionally permanently or detachably connected to a distal end 72 of condensation apparatus 60. Collection apparatus 100 generally comprises a collection chamber 102 configured to collect condensed liquid exhalate (condensate sample 103) from condensation apparatus 60. In the embodiment of FIG. 1; collection apparatus 100 also includes a connector portion 104. Connector portion 104 may be a conventional plastic pipe T-connector having a port 106 to permit venting of any uncondensed exhalate emerging from condensation apparatus 60, or air or other gases emanating from collection chamber 102 as is described in greater detail below. As shown in FIG. 1, port 106 may be selectively blocked by an egress port cap 108. In the embodiment of FIG. 1, the T-connector of connector portion 104 has a ⅜ inch internal diameter. Collection chamber 102 has a top end 112 and a bottom end 105 and is attached to connector portion 104, such as by frictionally engaging a stopper 110 disposed in top end 112 of collection chamber 102, as shown in FIG. 1. Stopper 110 may be a rubber stopper such as those often used with test tubes, or may be made of any other suitable material, and is frictionally disposed in a top end 112 of collection chamber 102. Stopper 110 may have a plurality of passages 114 through it to provide access to collection chamber 102, such as for the insertion of reagents, or testing or medical devices.

Collection chamber 102 may be a conventional plastic or glass test tube, as in the embodiment of FIG. 1, or any other container suitable for collecting condensed exhalate. Preferably, as in device 10, collection chamber 102 is removable and sealable such that a user has the option of collecting condensate in collection chamber 102 and transporting the same to a laboratory for evaluation. Collection chamber 102 may contain one or more solid, liquid or gaseous reagents, disposed either for direct communication with condensate sample 103, or in a separate, rupturable or openable reagent chamber 116. Reagent chamber 116 may be initially sealed and capable of being selectively opened at some point before, during, or after condensate collection to allow direct communication between the reagent and the condensate. The reagent could include any of a variety of dry or liquid substances which, when placed in contact with condensate sample 103, will provide an indication of the relevant chemical properties of the condensate. The decision as to which reagent to include in collection chamber 102 is driven by the chemical properties of interest. When device 10 is to be used for determining the acidity of condensed exhalate, for example, calorimetric pH reagents such as phenylphthalein, bromthymol blue or methyl red may be employed. It is also contemplated that reagent chamber 116 may contain one or more reagents capable of calorimetrically identifing concentrations of ions or other compounds in condensate sample 103, such as, but not limited to, nitrites and nitrates and acetic acid/acetate. One or more additional chambers 116 containing different reagents could also be included, such chambers being individually rupturable or openable for use in multi-step processes comprising a variety of assays.

Figure 3:
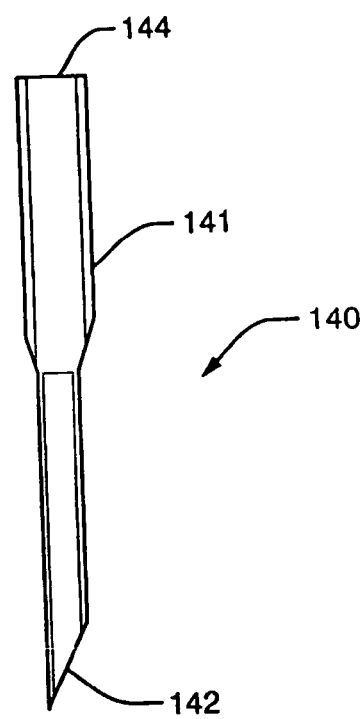
FIG. 3 is a plan view of a pipette that may be used in connection with the device of the present invention.
Figure 4:
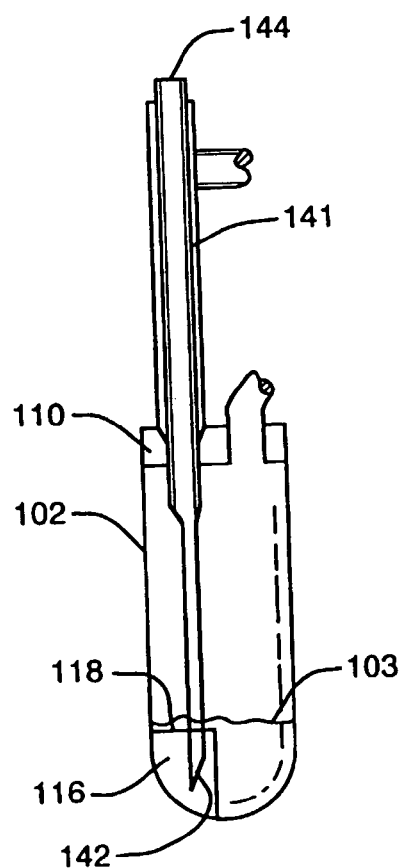
FIG. 4 is a cross-sectional view illustrating the positioning of pipette of FIG. 3 in the collection apparatus of FIG. 1.

In the embodiment of FIG. 1, reagent chamber 116 preferably is sealed but capable of being accessed, for example, by tip 142 of a pipette 140 (FIG. 3). Tip 142 is designed so that, when body portion 141 of pipette 140 is sealingly disposed in one of passages 114 in stopper 110 and has been fully inserted into collection chamber 102, as illustrated in FIG. 4, tip 142 will puncture or otherwise penetrate a top portion 118 of reagent chamber 116. When so disposed, pipette 140 also permits the passage of air (or other gases), whether introduced through first end 144 of pipette 140 or through a passage 114 in stopper 110, through condensate sample 103 and out of collection chamber 102 to atmosphere when pressure is applied, such as by a pressurized gas container, a pump 150, or through other pumping devices such as a syringe, pipette bulb, vacuum or other device, some potential uses of which are discussed in greater detail below. For example, top portion 118 of reagent chamber 116 may be made of a thin gauge plastic or other material which would be readily punctured by a sharp pipette tip 142 made of a material such as surgical steel. As one alternative to the configuration of pipette 140 presented in FIG. 3, first end 144 of pipette 140 may be disposed in close proximity to stopper 110 so that condensate is permitted to continue to travel through connector portion 104 and into condensate sample 103 when pipette 140 is in place.

Figure 5:
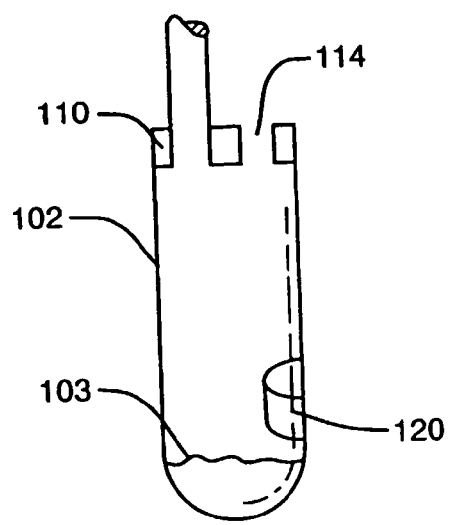
FIG. 5 is a cross-sectional view of the collection chamber of FIG. 1 containing a retainer.
Figure 6:
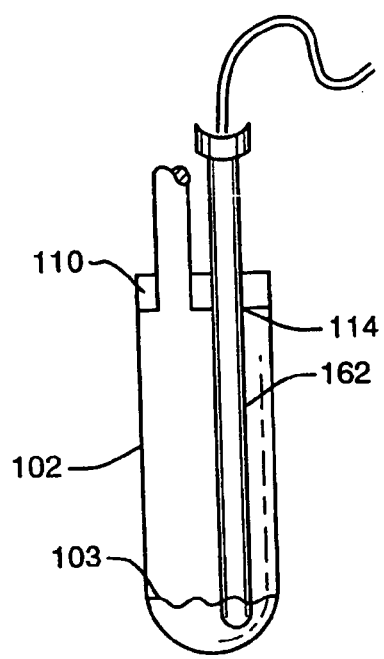
FIG. 6 is a cross sectional view illustrating the positioning of an electrode of an electronic monitor in the collection apparatus of FIG. 1.
Figure 7:
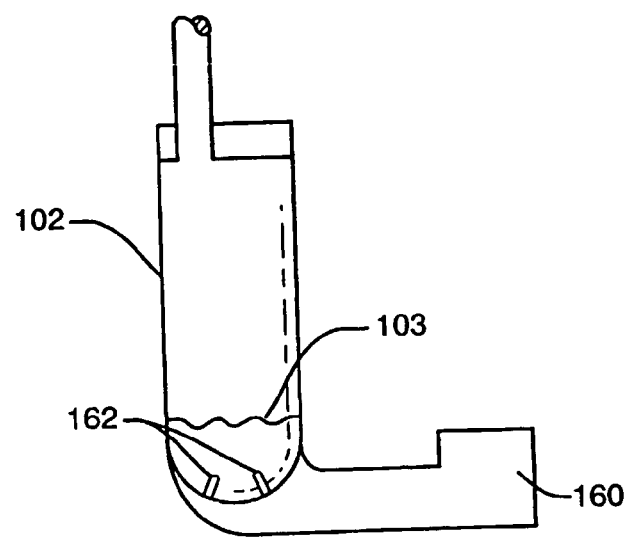
FIG. 7 is a cross sectional view illustrating another use of an electronic monitor in the collection apparatus of FIG. 1.

It will be appreciated that other means for determining properties of condensed exhalate may be employed as an alternative to the use of reagents disposed in a reagent chamber 116. As illustrated in FIG. 5, for example, collection chamber 102 may include a retainer 120 instead of a reagent chamber 116, retainer 120 holding a strip of material (not shown), which could be made of cloth, paper, or another suitable material, and which has a reagent embedded therein or coated thereon. When the level of condensate 103 in collection chamber 102 reaches the material being held by retainer 120, the material may change color to indicate the degree of acidity or other properties of the condensate. As an alternative to the use of a device such as retainer 120 or reagent chamber 116, a user of device 10 could simply dispose the chosen reagent or reagents through a pipette or otherwise through one of passages 114 once a sufficient volume of condensate has been collected for testing in collection chamber 102. As another exemplary alternative, as illustrated in FIG. 6, one of passages 14 may serve as an access site for one or more electrodes 162 of an electronic pH, acetic acid/acetate or other ion monitor 160 separate from device 10 and capable of determining selected chemical properties of condensate sample 103. As illustrated in FIG. 6, electrodes 162 may be disposed in collection chamber 102 so that as condensate accumulates, it will contact electrodes 162 of monitor 160. Alternatively, monitor 160 may be attached, by a screwable, snapable or other engagement mechanism, to collection chamber 102 such as in the manner illustrated in FIG. 7, in which electrodes 162 are disposed within collection chamber 102 for contact with condensate sample 103.

Collection chamber 102 preferably includes a measuring gradient 122, which is plainly visible to a user of device 10 so that the volume of collected condensate can be readily determined. Measuring gradient 122 is preferably etched or painted on collection chamber 102, which is preferably made of a transparent material such as clear glass or plastic so that when device 10 is held horizontally, the level of condensate may be viewed against measuring gradient 122.

The use of the device of the present invention will now be described with reference to the embodiment illustrated in FIG. 1, although it will be appreciated that the described method may be readily adapted to many other embodiments of the device. The condensation apparatus 60, preferably without insulator 78, is cooled, to a temperature, sufficiently low that condensation apparatus 60 will be capable of condensing exhalate when passed there through. Preferably, the temperature to which condensation apparatus 60 is cooled is below 0° C., most preferably −4 to −20° C. (the temperature capability of a conventional home freezer), but no lower than −80° C. A conventional home freezer is adequate to accomplish such cooling. Cooling in such a freezer typically requires approximately two hours, and preferably entails the sealing of passage 69 of condensation apparatus 60, at proximal end 62 and distal end 72, so that condensation is not permitted to accumulate therein. When cooling is complete, condensation apparatus 60 is removed from the freezer and insulator 78 is placed over condensation apparatus 60. Mouthpiece apparatus 20 is attached to proximal end 62 of condensation apparatus 60. Connector portion 104 of collection apparatus 100 is attached to distal end 72 of condensation apparatus 60. Port 106 is left open (i.e. with egress port cap 108 not engaging and blocking port 106).

A subject breaths through mouthpiece 26 with regular tidal breathing, or any other manner of breathing which may be desirable, for a sufficient time period for a useful volume of condensate to be collected in collection chamber 102 of collection apparatus 100. Although this time period varies based upon the type of testing means used, it is typically 2 to 10 minutes. During such breathing, device 10 may be tilted so that proximal end 22 of mouthpiece apparatus 20 is at a higher elevation than distal end 72 of condensation apparatus 60. This will allow gravity to assist the subject's breath in moving condensate forming in condensation apparatus 60 into collection apparatus 100. As exhalate is propelled into and through passage 69 in condensation apparatus 60 by the subject's breathing, vapor in the exhalate is condensed and the condensate flows through passage 69 and connector portion 104 and into collection chamber 102. Air in collection chamber 102 is displaced by condensate sample 103 and may pass out of collection chamber 102 through one or more of passages 114 in stopper 110, and through port 106 to atmosphere. Alternatively, egress port cap 108 may be used to block port 106, and one or more passages 114 in stopper 110 opened, such that displaced air may pass out of collection chamber 102 through such one or more passages 114.

Optionally, after a few drops of condensate have been obtained, the circuit formed by condensation apparatus 60 and collection apparatus 100 may be closed and means may be provided for recirculating exhalate through it in order to propel additional condensate through passage 69 and into collection chamber 102. As illustrated in FIG. 1, for example, a first tube 152 may be connected at a first end 154 to a passage 114 in stopper 110, and at a second end 156 to a first end 158 of a pump 150, thus connecting pump 150 to collecting chamber 102. Pump 150 may further be connected at a second end 163 to a first end 164 of a second tube 162, which may be connected at a second end 166 to passage 69 in condensation apparatus 60. With port 106 in connector portion 104 closed by cap 108 and all other ports 14 in stopper 110 closed, the actuation of pump 150 results in the recirculation of the exhalate through passage 69 of condensation apparatus 60, into collection chamber 102, through pump 150 and back through inner tube 66 (or in the reverse direction) repeatedly. Pump 150 is capable of driving condensate from the walls of inner tube 66 and into collection chamber 102. The use of pump 150 therefore augments (or optionally replaces) gravity in the collection of condensate. This makes possible a significant reduction in the time required for sampling (e.g. 2 minutes as opposed to 10 minutes) for the same recovery or condensate. The design or model of pump 150 is not critical, and it may be powered by AC, battery or other suitable power sources.

The device of the present invention may also be used for removing or standardizing the amounts of volatile and other substances within condensate sample 103 for increased measurement accuracy. This may be accomplished by bubbling atmospheric air (i.e. gas standardizing to standardize the amount of carbon dioxide in solution) or an inert gas such as argon or helium (i.e. degassing to remove acidifying carbon dioxide) through the condensate before or during the measurement of the acidic acid and/or acetate concentration(s) or other characteristics of the condensate. For example, the recirculation means previously described may, alternatively or in addition, be used as a means for removing or standardizing the amounts of volatile and other substances within the condensate. In one embodiment, device 10 may be configured for use with a pumping system such as that previously described comprising pump 150, first tube 152 and second tube 162, but with second end 166 of second tube 162 disconnected from passage 69 in condensation apparatus 60 and permitted to exhaust to the atmosphere, optionally through a filter. A pipette 140 or other such device, open to the atmosphere at a top end 144, may be inserted through one of passages 114 (similar to the manner illustrated in FIG. 4 in connection with inserting a pipette 140 into reagent chamber 116), sealing the same, and pipette tip 142 may extend into the condensate in collection chamber 102. With such a configuration, when pump 150 is activated, ambient air is drawn through pipette 140 and into collection chamber 102, through condensate sample 103, and through first tube 152, pump 150 and second tube 162, after which it is exhausted to atmosphere. The air is drawn through the condensate for a fixed period of time, typically between 1 and 10 minutes (this time period may be greater or lesser depending upon the particular requirements of the properties to be evaluated), thus rapidly equilibrating the condensate sample's carbon dioxide with ambient levels to assist in standardizing measurements.

Alternatively, a self-contained canister of inert or non-reactive gas, such as argon, helium or others, or a reactive gas selected as a reagent, may be connected to top end 144 of pipette 140. Air pump 150 may then be used to draw the gas through condensate sample 103, degassing the sample (i.e. removing volatile substances present in the sample) or allowing the reagent gas to react with the sample as part of a measurement process. In another potential embodiment, pump 150 may be disconnected and the inert or other gas bubbled through the condensate sample as the inert or other gas is emptied from a pressurized cylinder. It should also be noted that where a pipette 140 or other such device is disposed in collection chamber 102 as described, liquid or other reagents may be introduced to the condensate sample 103 through it, or it could be used for drawing condensate sample 103 out of chamber 102 with a syringe, pipette bulb, vacuum device or the like.

The degassing or gas standardizing is particularly valuable in gaining both reproducibility of results by adjusting the carbon dioxide levels in the condensate to a standard level (either zero, or an amount that is in equilibrium with normal air carbon dioxide levels) which is necessary for at least one known method of acetic acid/acetate assay. An added benefit of this technique is that it allows retention of the condensate, if desired, for further analysis for chemical content.

Depending upon the configuration of collection chamber 102 and the testing devices incorporated therein, condensate sample 103 may be tested for acetic acid and/or acetate concentration(s) or other properties during or following the collection of the sample. Collection chamber 102 may be provided with a reagent chamber 116 or retainer 120, along with appropriate reagents, for this purpose as previously described. In addition, or as an alternative, however, once an adequate condensate sample has been obtained, collection chamber 102 may be removed from device 10 and sealed for shipment to a laboratory equipped to test condensate sample 103 for acetic acid and/or acetate concentration(s) or other properties. Thus, collection chamber 102 preferably is disposable, or at least reusable. Of course, condensate sample 103 instead may be withdrawn from collection chamber 102 for shipment or testing, although this may be less cost-effective and cumbersome.

Figure 9:
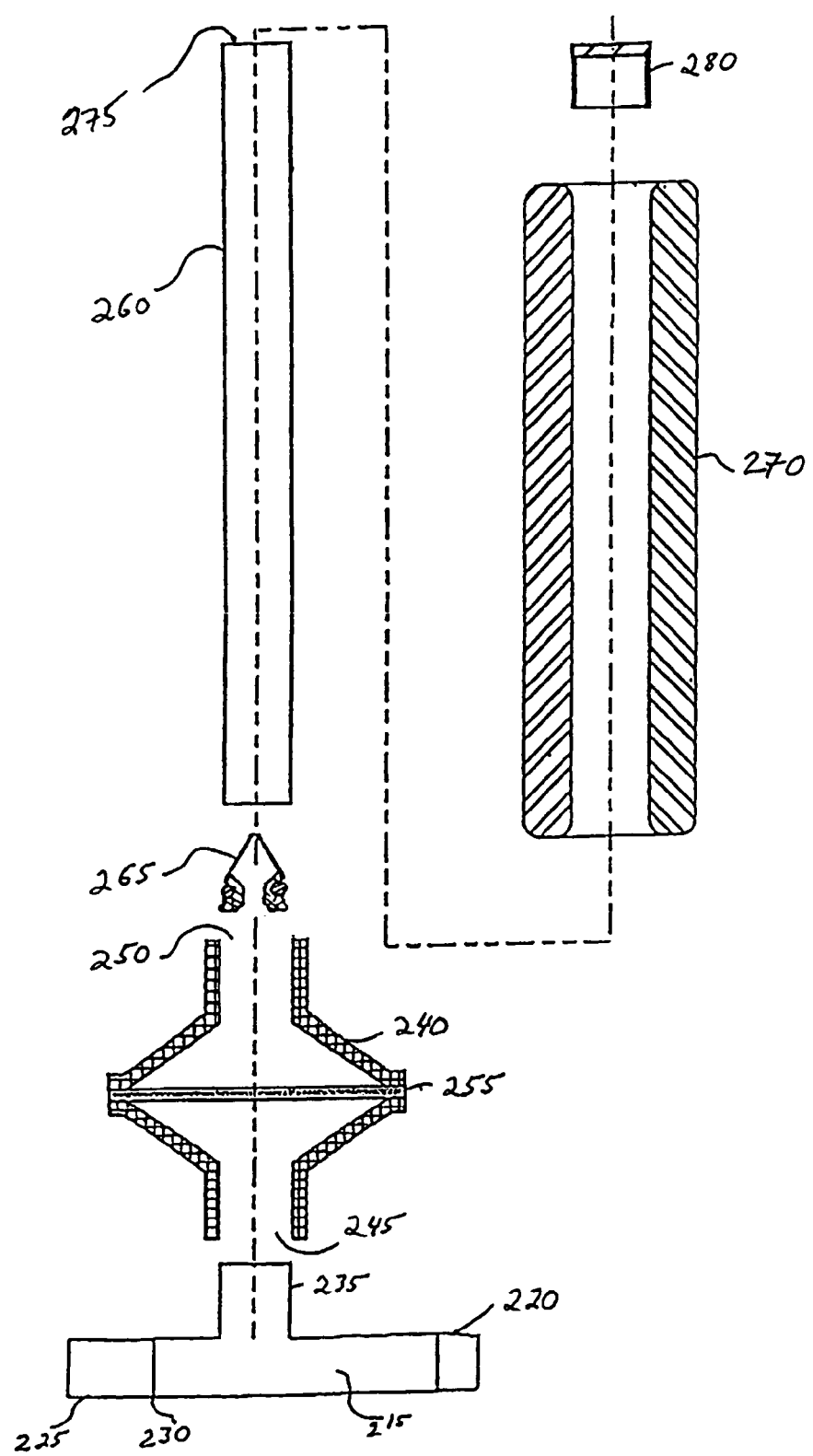
FIG. 9 is an alternative embodiment showing a center cross-sectional view of the individual components of the device in a disassembled state.

FIG. 9 shows an alternative embodiment of the present invention. FIG. 9 provides a center cross-sectional view along a center vertical axis of device 210 in a disassembled state from the component positioned vertically the lowest, mouthpiece 215, to that positioned highest, airtight cap 280. Airtight cap 280 is provided as part of device 210 for secure, retentive placement over open end 275 of collecting tube 260 after the method of the invention has been practiced but prior to storage and/or shipment of collecting tube 260 to a laboratory for analysis of condensate. Together with normally closed duckbill valve 265 (or other type of check valve), airtight cap 280 seals the condensate sample within collecting tube 260 and prevents any fluid exchange with matter or air outside of collecting tube 260. Airtight cap 280 may be formed from malleable plastic or another material, but its composition is not critical to practice of the invention so long as it provides a secure seal with open end 275 when placed there over. Collecting tube 260, duckbill valve 265 and airtight cap 280 together may form a disposable assembly which may be prepackaged for a single use ensuring no complicated cleaning or contamination arises from use of device 210.

As the first step in the method, referring again for visual reference to FIG. 9, a subject user places projection 220 of mouthpiece 215 between his or her lips and inhales. Duckbill valve 265 remains closed due to the bias of flaps 100 and air is admitted into mouthpiece 215 from projection 225 through check valve 230. The subject user then exhales. The stream of exhaled breath is blocked from egress out of projection 225 by check valve 230 and follows the path of least resistance upward through projection 235 into optional filter housing 240, through optional filter assembly 255 and into duckbill valve 265 where leaves 100 are caused to separate and open due to the air pressure allowing the exhaled breath to enter collecting tube 260. When exhalation is complete, leaves 100 return to their naturally biased closed position.

Accordingly, in this embodiment as described immediately above, the collecting tube 260 (collecting apparatus, container, or chamber) serves as the chamber for both the collecting tube as well as the condensation apparatus/function (condensation container, chamber, or tube). Moreover, the collecting tube also preferably contains means for testing the condensate to determine the chemical properties of the condensate. As described herein, such means may include, among other things, an electronic or other type of monitor, or a solid, liquid or gaseous reagent introduced to the condensate directly or indirectly. For example, the collection tube 260 may have a reagent chamber therein containing one or more reagents. It could be configured so that condensate collects in the collection chamber 260, eventually coming into contact with the reagent in the reagent chamber, or so that as condensate is produced, it enters the reagent chamber within the collection tube 260. Alternatively, the means for testing said condensate may comprise a retainer configured to hold a material, such as cloth or paper, in which one or more reagents are embedded or otherwise contained.

Still referring to FIG. 9, in yet another preferred embodiment, the present invention may be practiced without the need for a condensation function/step. Accordingly, the cooling sleeve 270 (or the condensation apparatus 60 as shown in the embodiment of FIG. 1) may be omitted. The collecting tube 260 (or collecting apparatus) is configured for directly trapping a subjects breath without the need for the condensation function/step. The collecting tube 260 comprised of a tube or container (open or closed container) with a reagent substance disposed therein or in communication therewith. The reagent or monitor may be disposed in a passage, receptacle, or holder (open or closed). The reagent substance being effective for trapping acetic acid and/or acetate concentration(s) from said subject's exhaled breath. By allowing the reagent (or sensor device) to directly process the exhalate as it is received in the device, this eliminates the step of collecting or accumulating the condensation. The collecting tube 260 may further comprise a device or means for (or may be in communication therewith a means for) testing the trapped acetic acid and acetate to determine concentration(s) thereof. An evaluating means for evaluating the acetic acid and/or acetate concentration may be provided for determining the presence, absence or status of a disease in the subject. It will be appreciated that other means for determining properties of the exhalate may be employed as an alternative to the use of reagents.

The following non-limiting Example is intended to further illustrate the present invention.

EXAMPLE

The pH of exhaled breath condensate has been shown to be acidic in patients during acute exacerbations of asthma. The initial source of the proton/acid load has not been elucidated. The aim of this study was to investigate if acetate (pKa=4.7) may contribute to breath condensate acidity in asthma.

This question was investigated in subjects with asthma admitted to hospital with exacerbations of their disease. Breath condensate samples were obtained within forty-eight hours after initiation of systemic corticosteroid therapy. Acetate was measured by spectrophotometry.

The samples from most (8/11) acute asthmatic patients had measurable acetate levels (median 8.5, range 0-24.5 mg/ml, n=11), in contrast to controls in which only two out of eighteen samples had detectable acetate (maximum 5.7 mg/ml). Exhaled breath condensate pH correlated negatively with acetate levels (r2=0.46, p<0.001), suggesting that this buffer system is a partial contributor to breath condensate pH in asthma.

This study demonstrates the presence of an unsuspected acidic buffer system present in the exhaled air of subjects with acute asthma. Possible sources for acetate in asthmatic breath include breakdown of acetylcholine at neuromuscular junctions, and action of aldehyde dehydrogenases. Acetate, a known vasoactive agent, may be involved in the pathology of asthma.

Exhaled air contains aerosolized particles, water vapor, and water-miscible volatile substances, all of which can be collected for assay by condensation of exhaled breath. Breath condensate assays are being increasingly recognized as a useful non-invasive tool to study airway biology (1). Unlike other methods of sampling airway fluid, this technique lends itself to safely collecting sample from patients even during acute exacerbations of asthma. Using this technique, we have shown that during exacerbations of asthma, breath condensate collected from patients is 1) highly acidic(2), and 2) deficient in ammonia (pKa=9.4) (in press). Given that ammonia concentrations are sometimes low in the presence of normal pH, we have concluded that ammonia deficiency is a necessary, but not sufficient characteristic of breath condensate acidity. We undertook theoretical and then empiric investigation to identify other species involved in this process.

The concentrations of ions in the human airway lining fluid in vivo are not well characterized, and not at all characterized during exacerbations of lung diseases. This is also the case for breath condensate ions. However, titration experiments suggested that there is a buffer system with a pKa just below 5 that is present only in low pH breath condensate samples. We therefore performed assays for acetate (pKa=4.7) and identified a prominent increase in airway production of this compound during exacerbations of asthma.

Study Subjects.

Study subjects had a history of asthma (n=11, age 21±3.0; 7 female), defined as three or more episodes of b-agonist responsive symptomatic airway obstruction, and were admitted to hospital with an acute exacerbation of their disease including wheezing, and with an inspiratory:expiratory ratio initially less than 1:2. Subjects who smoked, had concurrent pneumonia or any other chronic illness, or who had been treated with systemic corticosteroids for more than 48 hours prior to enrollment were excluded.

Control subjects (n=18, age 21±1.8; 11 female) consisted of healthy volunteers with no chronic or acute illness of any sort, recruited from among the general community. The protocol was approved by the institution's Human Investigations Committee.

Breath Condensate Collection.

Subjects performed quiet tidal oral breathing for 7 minutes into a pHTube™ breath condensate collection system (Respiratory Research, Inc. USA). Between 0.8 and 2.0 milliliters of fluid were collected during this period of time. If the patient was on oxygen, it was supplied through the inhalation port on the device. Asthmatic subjects were monitored with pulse-oximetry and additionally were attached to a cardiorespiratory monitor. The protocol calls for a cessation of collection if oxygen saturation were to fall by more than 3 percent.

Acetate Assay.

Samples in the pH Tubes were deaerated for five minutes with Argon (700 ml/min) per the manufacturer's instructions. One hundred microliter aliquots were withdrawn, degassed and the pH adjusted to 8±0.5 by careful addition of sub-microliter volumes of acetate-free sodium hydroxide. Acetate was measured spectrophotometrically by the Boehringer Mannheim Method (R-Biopharm Inc., Marshall, Mich.)(3). Briefly, acetate in undiluted 100 mL breath condensate samples was reacted in the presence of acetyl-CoA synthetase (ACS) with adenosine-5'-triphosphate (ATP) and coenzyme A (CoA) to form acetyl CoA. Acetyl CoA then was reacted with oxaloacetate to form citrate in the presence of citrate synthase. Availability of oxaloacetate was maintained by its de novo formation by NAD oxidation of added malate in the presence of L-malate dehydrogenase. The resultant NADH formed absorbs at 340 nm and is measured spectrophotometrically. This three-enzyme assay is specific for acetate. The lower detection limit as used in our laboratory is 5 mg/ml (83 mM acetate). The same assay was used to quantify levels of acetate in the hospital's nebulized medications.

Measurement of pH.

Breath condensate was deaerated to remove carbon dioxide by bubbling Argon at 700 ml/min through the collected condensate sample. pH was measured continuously using an Orion combination pH microelectrode attached to an Orion pH meter (Orion, Bedford Mass.). The pH of all samples stabilized within five minutes of beginning the deaeration process.

Analysis.

Data are presented as mean±S.E.M. where normally distributed, and otherwise as median and [range]. Comparison of acetate values between asthmatics and controls was made by Mann-Whitney Rank Sum because of the numerous control samples below the level of detection. Relationship between acetate and pH was assessed by linear regression. Results were considered significant at $p<0.05$.

Results

No patients suffered ill effects during the sampling procedure. There were no declines in oxygen saturation or evidence of clinical deterioration. There was no statistically significant difference between the age and sex distributions of the subjects and controls.

Figure 8:
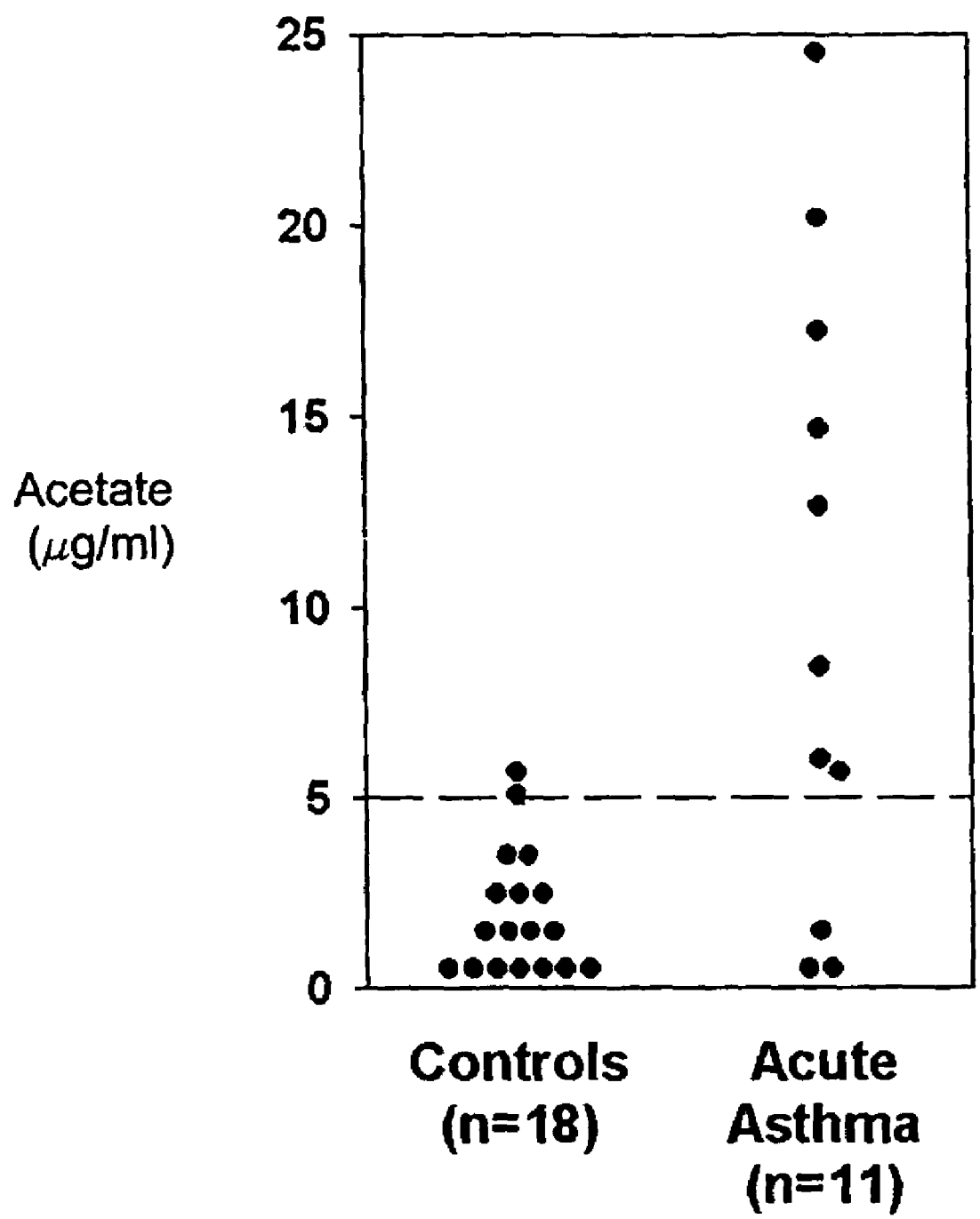
FIG. 8 is a graph showing acetic acid levels of condensate samples taken for control subjects and subjects suffering from acute asthma. Provided is acetate in exhaled breath condensate in controls and subjects with acute asthma. During tidal breathing, subjects exhaled through a cold condensation chamber for seven minutes. Condensed fluid from the breath was collected and assayed for acetate levels after deaeration with Argon to remove carbon dioxide. Patients with acute exacerbations of asthma exhale high concentrations of acetate (median 8.5 mg/ml [141 mM] in asthma, vs. undetectable in controls).

The median concentration of acetate in samples from acutely ill asthmatic subjects (median 8.5 mg/ml [0-24.5]) was significantly higher than in controls (undetectable, [0-5.7], $p<0.001$). Samples from sixteen out of eighteen controls had undetectable acetate, as opposed to asthmatic samples for which only three out of eleven were undetectable [FIG. 8]. No acetate was detectable in nebulized preparations used therapeutically for the treatment of acute asthma at our medical facility.

Acetate was not removed from breath condensate or water by the deaeration process at room or body temperature, even when the pH was below 5, when starting from concentrations of 10 mg/ml (167 mM) to 10 mg/ml (167 mM).

Assays for pH revealed a prominent acidity of the fluid from subjects with acute asthma (median pH of 5.3 [4.4-7.8]) compared to controls (pH=7.8 [6.8-8.1] consistent with our prior report(2). The pH correlated modestly with the concentrations of acetate ($r2=0.46$, $p<0.001$).

We have demonstrated that, in contrast to controls, acetate is present in the exhaled air of patients during acute exacerbations of asthma. This compound finding is a partial explanation for alterations in breath condensate pH.

To our knowledge, acetate and its conjugate acid, acetic acid, have never before been reported as potentially relevant to airway biochemistry outside of use for induction of cough(4). With a pKa of 4.7, this chemical pair nonetheless has the ability to profoundly influence pH in otherwise modestly buffered solutions. Challenges to the human airway with exogenous acids and with endogenous acid insults (such as in GERD and aspiration) cause cough(5), bronchoconstriction(6) and airway epithelial hyperpermeability (7). In cow trachea ex vivo(8) and human primary epithelial cells in vitro (unpublished observation) acid exposure at pH below 6.7 leads to epithelial cell damage and sloughing. Human ciliary function is poor below pH 6.8(9) and mucous viscosity can prominently increase(10). Eosinophils undergo necrosis within 24-48 hours of a mild acidic insult(2). All of these features are consistent with recent findings regarding the pathophysiology of asthma.

As a community, we have inadequate knowledge of airway lining fluid biochemistry in health, and essentially non-existent knowledge when it comes to acute disease states. Sampling of the airway lining fluid by filter paper or bronchoalveolar lavage is invasive and can be contraindicated in acute asthma. Breath condensate sampling provides an opportunity to collect fluid—derived at least in part from the lower airway—for performance of a wide array of assays. Although suffering from uncertain degrees of dilution (similar to bronchoalveolar lavage(11)) and still uncertain sites of origin (as for induced sputum(12, 13)), breath condensate studies performed since the early 1980's(14) have been revealing intriguing findings relevant to a variety of disease states.

Most of the compounds in breath condensate studied to date are thought to arise from particles of fluid aerosolized from the airway wall, diluted by water vapor condensation. The source of the acetate may also be aerosolized particles from the airway wall. Because acetic acid is a volatile acid with a high partition coefficient in water(15), it conceivably exists in vapor phase in an acidic airway to enter the breath condensate sample during the cold condensation process. Acetic acid would only arise in relevant amounts from a highly acidic and concentrated source fluid, because the conjugate base, acetate, cannot be considered volatile and stays in solution at neutral pH. Indeed, starting from a pH of 2.7 and 37° C. and 10 mg/ml (167 mM) acetic acid (1000-fold more concentrated than found in breath condensate), there is negligible loss of acetic acid from deionized water during deaeration, suggesting that volatility of this acid in relevant concentrations and temperatures is not likely to contribute significantly to condensate acetate levels.

Acetylcholine is catabolized by acetylcholinesterase to form choline, acetate and a proton. There is a reuptake mechanism for choline in the presynaptic neuron, but the fate of acetate is not established. We speculate that it can diffuse into the ALF and be available for aerosolization and, to a small extent, evaporation as acetic acid. Although the amount of acetylcholine released during exacerbations of asthma is not known, it is likely that it is overproduced in asthma(16), consistent with our current findings. Rough calculations of acetylcholine concentrations in ALF required to induce bronchospasm are consistent, to within a log order, with the amount of acetic acid exhaled by asthmatic subjects. Eosinophil major basic protein has been reported to competitively bind to the inhibitory presynaptic M2 receptor (17), suggesting a mechanism both of eosinophil-induced bronchial hyperreactivity and asthmatic acetylcholine and acetate overproduction.

A second possibility is that aldehyde dehydrogenases could be upregulated in the airway during exacerbations of asthma. For example, formaldehyde dehydrogenase upregulation in asthma has been postulated to be a mechanism for catabolism of the endogenous bronchodilator s-nitrosoglutathione(18, 19). In support of this hypothesis, we have found that intake of substantial quantities of ethanol by healthy volunteers (n=2, data not shown) can cause breath condensate acetate levels to subtly rise, likely by alcohol catabolism through acetaldehyde.

A final consideration is that microbial enzymes may contribute to exhaled acetate levels. Why bacterial contribution would occur specifically during asthma exacerbations is not readily explainable, however.

One intriguing aspect of this finding is that acetate is known to function both as a vasoconstrictor and vasodilator depending on system and dosing. Its presence in breath condensate at concentrations that have been shown to be vasoconstrictive(20) raises the possibility that this anion is involved in the smooth muscle pathophysiology of asthma.

In conclusion, we have identified inter alia a previously unrecognized component in the exhaled breath of patients suffering from exacerbations of asthma, and other respiratory and non-respiratory disease. The concentration of the acetic acid/acetate buffer system in breath condensate correlates modestly with the pH of the fluid. We speculate that the presence of this buffer may result from increased acetylcholine release and breakdown in the asthmatic airway, or alterations in enzyme activities relating to aldehyde metabolism. The possibility that acetate is involved in the pathophysiology of asthma is under investigation.

As will be appreciated in view of the foregoing, the device and method of the invention provide a simple, rapid, non-invasive approach for diagnosing and managing treatment of respiratory disease. The device and method have been shown to provide reproducible results. The device of the present invention provides not only the ability of a user to collect condensate from a subject, but to also test the condensate for acetic acid and/or acetate indicative of asthma (or potentially other diseases) during or immediately following condensate collection. In addition, the device may be configured in detachable parts. This feature not only permits the replacement of parts as required, without replacing the entire device, but also permits the easy cleaning of the condensation apparatus and placement of the condensation apparatus alone in a home freezer, or other cooling device having a limited space, prior to use. In addition, the collection chamber of the collection apparatus may be detached if desired following condensate collection, and shipped to an off-site location for primary or additional testing or analysis. Among other things, these features make the device of the present invention ideal for home use, as well as for use in a clinic, hospital or emergency room setting.

Additionally, the present invention device and method may be practice with the condensation and collection tube being the same general region or container.

Moreover, the present invention device and method may be practiced by measuring the exhaled breath directly without collecting the resultant condensate.

It is believed that the many advantages of the present invention will now be apparent to those skilled in the art. It will also be apparent that a number of variations and modifications may be made thereto without departing from the spirit and scope of the foregoing written description. Accordingly, the foregoing description is to be construed as illustrative only, rather than limiting. The present invention is limited only by the scope of the following claims.

REFERENCES

The following references as cited throughout this document are hereby incorporated by reference in their entirety herein.

1. Kharitonov S A, Barnes P J. Exhaled markers of pulmonary disease. Am J Respir Crit Care Med 2001; 163(7):1693-722.

2. Hunt J F, Fang K, Malik R, Snyder A, Malhotra N, Platts-Mills T A, Gaston B. Endogenous airway acidification. Implications for asthma pathophysiology. Am J Respir Crit Care Med 2000; 161(3 Pt 1):694-9.

3. Bergmeyer H U. Methods of Enzymatic Analysis. 2 ed. New York: Weinheim/Academic Press, 1974.

4. Mochizuki H, Shimizu T, Maeda S, Tokuyama K, Morikawa A, Kuroume T. Relationship between ultrasonically nebulized distilled water-induced bronchoconstriction and acetic acid-induced cough in asthmatic children. J Allergy Clin Immunol 1995; 96(2):193-9.

5. Shimizu T, Mochizuki H. Tokuyama K, Morikawa A. Relationship between the acid-induced cough response and airway responsiveness and obstruction in children with asthma. Thorax 1996; 51(3):284-7.

6. Fine J M, Gordon T, Sheppard D. The roles of pH and ionic species in sulfur dioxide- and sulfite-induced bronchoconstriction. Am Rev Respir Dis 1987; 136(5):1122-6.

7. Ohrui T, Yamaya M, Suzuki T, Sekizawa K, Funayama T, Sekine H, Sasaki H. Mechanisms of gastric juice-induced hyperpermeability of the cultured human tracheal epithelium. Chest 1997; 111(2):454-9.

8. Holma B, Lindegren M, Andersen J M. pH effects on ciliomotility and morphology of respiratory mucosa. Arch Environ Health 1977; 32(5):216-26.

9. Luk C K, Dulfano M J. Effect of pH, viscosity and ionic-strength changes on ciliary beating frequency of human bronchial explants. Clin Sci 1983; 64(4):449-51.

10. Holma B, Hegg P O. pH- and protein-dependent buffer capacity and viscosity of respiratory mucus. Their interrelationships and influence on health. Sci Total Environ 1989; 84:71-82.

11. Ward C, Duddridge M, Fenwick J, Williams S, Gardiner P V, Hendrick D J, Walters E H. The origin of water and urea sampled at bronchoalveolar lavage in asthmatic and control subjects. Am Rev Respir Dis 1992; 146(2):444-7.

12. Holz O, Kips J, Magnussen H. Update on sputum methodology. Eur Respir J 2000; 16(2):355-9.

13. Gershman N H, Liu H, Wong H H, Liu J T, Fahy J V. Fractional analysis of sequential induced sputum samples during sputum induction: evidence that different lung compartments are sampled at different time points. J Allergy Clin Immunol 1999; 104(2 Pt 1):322-8.

14. Sidorenko G I, Zborovskii E I, Levina D I. [Surface-active properties of the exhaled air condensate (a new method of studying lung function)]. Ter Arkh 1980; 52(3): 65-8.

15. Budavari S. The Merck Index. 12 ed. Whitehouse Station, N.J.: Merck Research Laboratories, 1996.

16. de Jongste J C, Jongejan R C, Kerrebijn K F. Control of airway caliber by autonomic nerves in asthma and in chronic obstructive pulmonary disease. Am Rev Respir Dis 1991; 143(6):1421-6.

17. Gleich G J, Jacoby D B, Fryer A D. Eosinophil-associated inflammation in bronchial asthma: a connection to the nervous system. Int Arch Allergy Immunol 1995; 107(1-3):205-7.

18. Liu L, Hausladen A, Zeng M, Que L, Heitman J, Stamler J S. A metabolic enzyme for S-nitrosothiol conserved from bacteria to humans. Nature 2001; 410(6827): 490-4.

19. Fang K, Johns R, Macdonald T, Kinter M, Gaston B. S-nitrosoglutathione breakdown prevents airway smooth muscle relaxation in the guinea pig. Am J Physiol Lung Cell Mol Physiol 2000; 279(4):L716-21.

20. Altura B M, Gebrewold A. Failure of acetaldehyde or acetate to mimic the splanchnic arteriolar or venular dilator actions of ethanol: direct in situ studies on the microcirculation. Br J Pharmacol 1981; 73(3):580-2.

What is claimed is:

1. A method for assessing a disease in a subject, said method comprising:
    collecting condensate from a subject's breath, said condensate having an acetic acid or acetate concentration or both an acetic acid and acetate concentration;
    testing said condensate to determine said acetic acid or acetate concentration or both said acetic acid and acetate concentrations; and
    evaluating said acetic acid or acetate concentration or both said acetic acid and acetate concentrations to determine the presence, absence or status of a disease in the subject.

2. The method of claim 1, wherein said disease is a respiratory disease.

3. The method of claim 2, wherein said step of evaluating said acetic acid or acetate concentration or both said acetic acid and acetate concentrations to determine the presence, absence or status of a respiratory disease in the subject comprises determining the presence, absence or status of an inflammatory respiratory disease.

4. The method of claim 3, wherein said step of determining the presence, absence or status of an inflammatory respiratory disease comprises determining the presence, absence or status of asthma.

5. The method of claim 2, wherein said step of determining the presence, absence or status of a respiratory disease comprises determining the presence, absence or status of a respiratory disease that is a member of the group consisting of asthma, bronchiolitis, chronic obstructive pulmonary, bronchiectasis, common cold, cystic fibrosis, smoking induced diseases, tuberculosis, and occupational lung diseases.

6. The method of claim 1, wherein said step of determining said acetic acid or acetate concentration or both acetic acid and acetate concentrations of said condensate comprises using means for testing said condensate to determine said acetic acid or acetate concentration or both said acetic acid or acetate concentrations.

7. The method of claim 6, wherein said step of using means for testing said condensate to determine said acetic acid or acetate concentration or both said acetic acid and acetate concentrations comprises using at least one of at least one electronic acetic acid monitor and at least one acetate monitor and at least one acetic acid and acetate monitor.

8. The method of claim 6, wherein said testing means comprise at least one acetic acid selective electrode.

9. The method of claim 6, wherein said step of using means for testing said condensate to determine said acetic acid or acetate concentration or both said acetic acid and acetate concentrations comprises using at least one ultraviolet/visible spectroscopy system.

10. The method of claim 6, wherein said step of using means for testing said condensate to determine said acetic acid or acetate concentration or both said acetic acid or acetate concentrations comprises using at least one of at least one mass spectroscopy system and at least one gas chromatography mass spectroscopy system.

11. The method of claim 6, wherein said step of using means for testing said condensate to determine said acetic acid or acetate concentration or both said acetic acid and acetate concentrations comprises using at least one artificial nose system.

12. The method of claim 6, wherein said step of using means for testing said acetic acid or acetate or both said acetic acid and acetate condensate to determine said acetic acid or acetate concentration or both said acetic acid and acetate concentrations comprises introducing at least one reagent to said condensate.

13. The method of claim 1, wherein said condensate comprises volatile substances, and said method further comprises standardizing said volatile substances within said condensate prior to said testing step.

14. The method of claim 13, wherein said step of standardizing said volatile substances within said condensate comprises a gas standardizing step.

15. The method of claim 13, wherein said step of standardizing said volatile substances within said condensate comprises a degassing step.

16. The method of claim 15, wherein said degassing step comprises introducing an inert gas to said condensate.

17. The method of claim 1, wherein said step of collecting condensate from a subject's breath comprises collecting condensate from a human or an animal subject.

18. The method of claim 1, wherein said step of collecting condensate from a subject's breath comprises condensing breath that has been exhaled through the subject's mouth.

19. The method of claim 1, wherein said step of collecting condensate from a subject's breath further comprises condensing breath that has been exhaled through the subject's nose or both nose and mouth.

20. The method of claim 1, wherein said step of collecting condensate from a subject's breath further comprises condensing breath that has been exhaled through the subject's endotrachial tube or tracheostomy tube.

21. The method of claim 1, wherein said step of collecting condensate from a subject's breath comprises:
    introducing the subject's breath into a condensation apparatus, said condensation apparatus producing a condensate from said breath; and
    moving said condensate into a collection apparatus.

22. The method of claim 21, wherein said step of moving said condensate into a collection apparatus comprises moving said condensate by force of gravity.

23. The method of claim 21, wherein said step of moving said condensate into a collection apparatus comprises moving said condensate using a pump.

24. The method of claim 1, wherein said step of collecting condensate from a subject's breath comprises:
    introducing a sample of said breath into a condensation apparatus capable of producing a condensate from said breath; and
    collecting said condensate produced by said condensation apparatus in said condensation apparatus.

25. The method of claim 1, wherein said step of collecting condensate from a subject's breath comprises:
    providing a cooled condensation apparatus; and
    introducing a sample of said breath into said cooled condensation apparatus.

26. The method of claim 25, wherein said cooled condensation apparatus has a temperature at least as low as about 10° C.

27. The method of claim 25, wherein said cooled condensation apparatus has a temperature at least as low as about −80 C.

28. The method of claim 1, wherein said step of evaluating said acetic acid or acetate concentration or both said acetic acid and acetate concentrations to determine the presence, absence or status of a disease in the subject comprises evaluating said acetic acid or acetate concentration or both said acetic acid and acetate concentrations to diagnose at least one of at least one respiratory disease and at least one non-respiratory disease in the subject.

29. The method of claim 28, wherein said step of evaluating said acetic acid or acetate concentration or both said acetic acid and acetate concentrations to determine the presence, absence or status of at least one of at least one respiratory disease and at least one non-respiratory disease in the subject comprises evaluating said acetic acid or acetate concentration or both said acetic acid and acetate concentrations to determine the severity of said respiratory and non-respiratory disease in the subject.

30. The method of claim 28 wherein said step of evaluating said acetic acid or acetate concentration or both said acetic acid and acetate concentrations to determine the presence, absence or status of at least one of at least one respiratory disease and at least one non-respiratory disease in the subject comprises evaluating said acetic acid or acetate concentration or both said acetic acid and acetate concentrations to determine whether a course of treatment for said respiratory and non-respiratory disease in the subject should be started, altered or discontinued.

31. The method of claim 28, wherein said step of evaluating said acetic acid or acetate concentration or both said acetic acid and acetate concentrations to determine the presence, absence or status of at least one of at least one respiratory disease and at least one non-respiratory disease in the subject comprises evaluating said acetic acid or acetate concentration or both said acetic acid and acetate concentrations to predict an impending exacerbation of said respiratory or non-respiratory disease in the subject.

32. A method for assessing asthma in a subject, comprising:
providing a device comprising a mouthpiece apparatus, a condensation apparatus and a collection apparatus;
receiving a subject's breath in said mouthpiece apparatus;
condensing said breath in said condensation apparatus to form a condensate;
collecting said condensate in said collection apparatus;
testing said condensate within said collection apparatus to determine acetic acid or acetate concentration or both said acetic acid and acetate concentrations; and
evaluating said acetic acid or acetate concentration or both said acetic acid and acetate concentrations to determine the presence, absence or status of asthma in the subject.

33. A method for assessing asthma in a subject, comprising:
providing a device comprising a mouthpiece apparatus and a condensation apparatus;
receiving a subject's breath in said mouthpiece apparatus;
condensing said breath in said condensation apparatus to form a condensate;
collecting said condensate in said condensing apparatus;
testing said condensate within said condensation apparatus to determine acetic acid or acetate concentration or both said acetic acid and acetate concentrations; and
evaluating said acetic acid or acetate concentration or both said acetic acid and acetate concentrations to determine the presence, absence or status of asthma in the subject.

34. A device for assessing a disease in a subject, said device comprising:
a mouthpiece apparatus configured to receive breath from a subject;
a condensation apparatus configured for operative connection to said mouthpiece apparatus, and being further configured to condense the subject's breath and produce a condensate having acetic acid or acetate or both said acetic acid and acetate; and
a collection apparatus configured for operative connection to said condensation apparatus, said collection apparatus comprising a collection chamber containing means for testing said condensate to determine said acetic acid or acetate concentration or both said acetic acid and acetate concentrations, wherein the subject's breath may be received, condensed and evaluated in a single device to determine the presence, absence or status of a disease in the subject.

35. The device of claim 34, wherein said means for testing said condensate comprises a reagent disposed within said collection chamber.

36. The device of claim 35, wherein said reagent is a solid reagent.

37. The device of claim 35, wherein said condensate has acetic acid or acetate concentration or both said acetic acid and acetate concentrations and said reagent is useful for measuring said acetic acid or acetate concentration or both said acetic acid and acetate concentrations of said condensate.

38. The device of claim 35, wherein said means for testing said condensate comprises a reagent chamber containing at least one reagent.

39. The device of claim 35, wherein said means for testing said condensate comprises a retainer configured to hold a material, said material comprising a reagent.

40. The device of claim 34, wherein said means for testing said condensate comprises an electrode of an electronic monitor.

41. The device of claim 40, wherein said electronic monitor is configured to connect to said collection chamber.

42. The device of claim 34, wherein said collection chamber is detachable and disposable.

43. The device of claim 42, wherein said collection chamber comprises a plastic test tube.

44. The device of claim 34, wherein said collection chamber comprises a measuring gradient in communication therewith.

45. The device of claim 34, wherein said mouthpiece apparatus comprises proximal end, a distal end, and a mouthpiece disposed at said proximal end of said mouthpiece apparatus.

46. The device of claim 45, wherein said mouthpiece apparatus further comprises a first one-way valve configured to permit air to be drawn into said mouthpiece apparatus, and a second one-way valve configured to permit air to pass from said mouthpiece to said distal end of said mouthpiece apparatus.

47. The device of claim 46, wherein said mouthpiece apparatus further comprises a particle filter disposed between said mouthpiece and said distal end of said mouthpiece apparatus.

48. The device of claim 34, wherein said condensation apparatus comprises an inner tube surrounded by an insulator.

49. The device of claim 48, wherein:
said inner tube has an outer surface; and
said condensation apparatus further comprises an outer tube disposed between said inner tube and said insulator, said outer tube having an inner surface, and said inner surface of said outer tube and said outer surface of said inner tube defining a heat transfer chamber.

50. The device of claim 49, wherein said heat transfer chamber contains a cooling material.

51. The device of claim 50, wherein said outer tube has a first port therein providing access to said heat transfer chamber, and a second port therein providing access to said heat transfer chamber, wherein said cooling material may be inserted into said heat transfer chamber through said first port and removed through said second port.

52. The device of claim 49, wherein said inner tube is made of aluminum, said outer tube is made of plastic and said insulator is made of foam plastic.

53. The device of claim 34, wherein said collection apparatus further comprises a connector portion configured to connect said collection chamber to said condensation apparatus.

54. The device of claim 53, wherein said connector portion comprises a T-connector having a first T-portion and a second T-portion, said first T-portion being configured to connect said T-connector to said collection chamber and said second T-portion providing a port to atmosphere, wherein uncondensed breath passing through said condensation apparatus and into said T-connector may vent to atmosphere.

55. The device of claim 54, wherein said device further comprises an apparatus to standardize volatile substances within said condensate.

56. The device of claim 55, wherein said apparatus to standardize volatile substances within said condensate comprises a degassing apparatus.

57. The device of claim 56, wherein said degassing apparatus comprises a pump.

58. A device for assessing a disease in a subject, said device comprising:
a mouthpiece apparatus configured to receive breath from a subject;
a condensation apparatus configured for operative connection to said mouthpiece apparatus, and being further configured to condense and collect the subject breath and produce a condensate having acetic acid or acetate concentration or both said acetic acid and acetate concentrations; and
said condensation apparatus comprising a means for testing said condensate to determine said acetic acid or acetate concentration or both said acetic acid and acetate concentrations.

59. The device of claim 58, wherein said means for testing said condensate comprises a reagent disposed within said collection chamber.

60. The device of claim 58, wherein said means for testing said condensate comprises an electrode of an electronic monitor.

61. The device of claim 58, wherein said condensation apparatus is detachable and disposable.

62. A method for assessing a disease in a subject, said method comprising:
said subject exhaling through a measuring device or substance, said measuring device or substance effective for detecting acetic acid or acetate or both acetic acid and acetate;
testing said detected acetic acid or acetate or both said detected acetic acid and acetate to determine said acetic acid or acetate concentration or both said acetic acid or acetate concentrations; and
evaluating said acetic acid or acetate concentration or both said acetic acid and acetate concentrations to determine the presence, absence or status of a disease in the subject.

63. The method of claim 62, wherein said measuring device or substance is a reagent, said reagent effective for trapping acetic acid or acetate or both acetic acid and acetate.

64. The method of claim 63, wherein said reagent is a solution or a solid or both.

65. The method of claim 64, wherein said reagent is a base.

66. The method of claim 65, wherein said base comprises Sodium Hydroxide, or any of several potential single or combined compounds that together have the ability to consume protons and thereby alkalinize a water.

67. The method of claim 62, wherein said measuring device or substance is a spectroscopy system, electrode, chemical reagent strip or artificial nose for detecting acetic acid or acetate or both acetic acid and acetate.

68. The method of claim 62, wherein said disease comprises at least one of at least one respiratory disease and at least one non-respiratory disease in the subject.

69. A device for assessing a disease in a subject, said device comprising:
a mouthpiece apparatus configured to receive breath from a subject;
a measuring device or substance configured for operative connection to said mouthpiece apparatus, said measuring device or substance effective for detecting acetic acid or acetate concentration or both said acetic acid and acetate concentrations from said subject's breath;
a means for testing said trapped acetic acid and acetate to determine said acetic acid or acetate concentration or both said acetic acid and acetate concentrations; and
an evaluating means for evaluating said acetic acid or acetate concentration or both said acetic acid and acetate concentrations to determine the presence, absence or status of a disease in the subject.

70. The device of claim 69, wherein said measuring device or substance is a reagent, spectroscopy system, electrode, or artificial nose for detecting acetic acid or acetate or both acetic acid and acetate.

71. The method of claim 69, wherein said disease comprises at least one of at least one respiratory disease and at least one non-respiratory disease in the subject.

* * * * *